United States Patent
Meier et al.

(10) Patent No.: US 9,449,520 B2
(45) Date of Patent: Sep. 20, 2016

(54) SYSTEM AND METHOD FOR VERIFYING VIEWING OF MULTIMEDIA RENDERING OF INVESTIGATOR MEETING PREFATORY TO CLINICAL TRIAL PARTICIPATION

(76) Inventors: Alden Meier, Los Angeles, CA (US); Edwin Sahakian, Glendale, CA (US); Dave Young, Los Angeles, CA (US)

(*) Notice: Subject to any disclaimer, the term of this patent is extended or adjusted under 35 U.S.C. 154(b) by 621 days.

(21) Appl. No.: 12/449,791

(22) PCT Filed: Feb. 27, 2008

(86) PCT No.: PCT/US2008/002599
§ 371 (c)(1),
(2), (4) Date: Aug. 26, 2009

(87) PCT Pub. No.: WO2008/106172
PCT Pub. Date: Sep. 4, 2008

(65) Prior Publication Data
US 2010/0070861 A1   Mar. 18, 2010

Related U.S. Application Data

(60) Provisional application No. 60/903,662, filed on Feb. 27, 2007.

(51) Int. Cl.
| | |
|---|---|
| G06F 3/00 | (2006.01) |
| G09B 5/00 | (2006.01) |
| G09B 7/00 | (2006.01) |
| G06F 3/01 | (2006.01) |

(52) U.S. Cl.
CPC .. G09B 5/00 (2013.01); G09B 7/00 (2013.01)

(58) Field of Classification Search
CPC .................................. G09B 5/00; G09B 7/00
USPC ................................ 715/730, 751, 780, 829
See application file for complete search history.

(56) References Cited

U.S. PATENT DOCUMENTS

| | | | | |
|---|---|---|---|---|
| 6,615,020 | B2 * | 9/2003 | Richter et al. | 434/350 |
| 2003/0113700 | A1 * | 6/2003 | Simon | 434/350 |
| 2004/0078220 | A1 * | 4/2004 | Jackson | 705/2 |
| 2004/0191744 | A1 * | 9/2004 | Guirguis | 434/322 |
| 2006/0184535 | A1 * | 8/2006 | Kaluskar et al. | 707/10 |
| 2007/0196808 | A1 * | 8/2007 | Call | 434/350 |
| 2008/0108035 | A1 * | 5/2008 | Warda | 434/335 |
| 2008/0222678 | A1 * | 9/2008 | Burke et al. | 725/44 |
| 2008/0225757 | A1 * | 9/2008 | Johnson | 370/260 |
| 2010/0037320 | A1 * | 2/2010 | Moed et al. | 726/24 |

* cited by examiner

Primary Examiner — Nicholas Augustine

(57) ABSTRACT

A system and method providing passive verification of participant—typically a physician—exposure to Material equivalent to attendance at an Investigator Meeting prefatory to Clinical Trial is taught. The invention provides for rendering media capture of Investigator Meeting education into computer deliverable sessions, and further into segments, where segments are the product of randomly generated visual requests to which participant need provide response in some prescribed time interval to confirm visual attention to Material. To ensure participant visual exposure to Material, during computer mediated display of Material, visual prompts appear at random points in the display. For any successful participant response, session advances, and in absence of successful response, display of Material resets to last successful response point in Material. In an alternate embodiment, groups of viewers may be tracked corresponding to a group viewing of Material. The system provides real-time tracking of completion of visual exposure to Investigator Meeting Material and enables Clinical Trial sponsor to dynamically update enrolled participant data, and actively encourage physician completion of Investigator Meeting equivalent attendance, so as to expedite Clinical Trial launch.

1 Claim, 7 Drawing Sheets

SYSTEM AND METHOD FOR VERIFYING VIEWING OF MULTIMEDIA RENDERING OF INVESTIGATOR MEETING PREFATORY TO CLINICAL TRIAL PARTICIPATION

RELATED APPLICATIONS

This application claims priority from U.S. provisional application 60/903,662 by the same inventors, filed Feb. 27, 2007 and which is incorporated by reference in its entirety.

FIELD OF USE

This invention relates to computer based learning delivery systems and more specifically concerns a means to verify viewer compliance with viewing requirements. In a specific embodiment, the invention relates to physicians ("investigators") complying with requirements to participate as investigators in clinical trials.

BACKGROUND

Computer based learning delivery systems have been in existence almost since the availability of computers and related network technologies. Computerized learning delivery systems have progressed to a point where, in conjunction with advances in network and telecommunications technology, online distance learning is practical. The Internet has made it possible to deliver rich multimedia training material that contains video, text, and graphics to viewers who are widely geographically dispersed. Online systems can deliver powerful, effective training materials to many viewers at virtually any location, at any time. This allows the expertise of teachers and/or "knowledge experts" to be captured once and delivered many times to virtually unlimited numbers of viewers at their convenience.

Government, corporations and educational institutions have implemented learning and/or training programs over the Internet. Many types of network or Internet on-line training are now possible using this technology. Training of this sort includes professional education where the professional must complete some required number of hours of training in the specified area of learning. However, an obvious problem with online learning delivery systems is a means of verifying that the viewer has actually watched all of the materials in the prescribed curriculum. A viewer may simply elect to not watch the training at all or may simply start the training and allow the training to automatically progress while they are otherwise occupied or physically away from the computer or terminal where the training is being delivered. In either case, the viewer has avoided meeting the basic requirement that they actually watch all of the training materials. It should be noted that the requirement to watch the training material is separate and distinct from the need to ensure that the viewer demonstrates retained knowledge and understanding of the materials presented.

Because it is difficult to verify that a viewer has actually viewed all of the required materials, many companies, governments, or regulatory authorities have simply not permitted distance training to be used for some forms of training. Without the ability to verify that the viewer has in fact viewed all of the required material, it is impossible to ensure that the viewer has met the minimum requirements for the training. What is needed is a means to verify viewer compliance with viewing requirements associated with on-line or network mediated training.

U.S. Pat. No. 6,928,260, Betz, et al ("Betz") allows for bidirectional communication between the educator and the viewer using an audio controlling mechanism. The viewer is not permitted to advance during the time that the audio file is "played" by the plug-in and/or browser. As the rate of advancement of the educational material presented to the viewer is controlled by the system, the system insures that the viewer "attends" the course for a minimum period of time. The system prevents the viewer from skipping, or fast forwarding the material. Practically speaking, Betz only teaches a system to control the pace and advancement of the training, and permits confirmation the materials were played or "delivered" to a User's computing device. However, the Betz system and method does not ensure that the User/viewer is, in fact, actually listening to or viewing the training materials that are being "delivered."

It is useful to consider the invention in the preferred embodiment: verifying that physicians intending to be "investigators" in a Clinical Trial view a recording (audio visual presentation) of the Investigator Meeting if they did not attend the live event. Each and every physician in a clinical trial must receive the protocol instructions and related information, and the protocol instructions are taught and discussed at an Investigator Meeting. A Clinical Trial launch could be delayed if an insufficient number of physicians have attended an Investigator Meeting. Thus it has become increasingly important to duplicate the substantive experience of exposure to the material presented at the live event (i.e. the Investigator Meeting).

It can be appreciated that the physicians who elect to view the recorded Investigator Meeting rather than attend the live event are subjected to no tests, nor are the physicians who elect to attend the live event.

What is needed is means to ensure that a viewer is attending to the media, including circumstances in which media is delivered over a network, including the World Wide Web or the Internet. What is further needed is a means to track partial completion of required viewing, and presentation of any remaining materials to be viewed, so that viewer is reliably tracked, and compliance documented.

SUMMARY

The present invention meets at least all of the recited needs. The invention taught herein provides a system and method to ensure that the viewer is actually present and watching the materials, the media or audio visual content, by requiring successful input from the viewer at random intervals during the presentation of the training material in such a manner as to confirm that they are actually at the computer or terminal and are actively viewing the materials. The system requires viewer input to occur within a pre-set period of time after the prompt.

In the event that the viewer fails to successfully perform the required input within the provided time period, the system will pause the training and wait for the viewer to return. Once the viewer resumes their training, the system restarts the training at the time point of the last successful data input (or the beginning of the training if no input has been required up to that point) and requires the viewer to watch the training from that point again.

In addition to requiring random input from the viewer, the system automatically keeps track of all of the material that has been presented to ensure that all of the training material has actually been viewed before certifying that they have completed the training segment.

Each time a viewer initiates a training session, the system authenticates that the person signing in is in fact the person who is required to take the training.

By tracking the material that has been presented to a viewer and requiring the authenticated viewer to enter input at random intervals during the presentation, the system forces the viewer to be present at the computer and ensures that all of the training materials have been watched. If the viewer fails to enter the required input within the required amount of time, the System requires the viewer to re-watch the presentation from the time of the last successful input.

The System is comprised of the Server, the Launcher, and the Player. The Server is the system that contains the database and all of the data needed to support the launcher and the player (see below). The server also contains all of the code that supports the launcher and the player.

The Launcher is a page where all of the Topics and Presentations that make up a meeting (or event) are organized and presented to the user. It is primarily an organized view of the meeting or event content in a logical order and allows the user to navigate. The Launcher is where the user can see which segments they have viewed and which segments come next. The launcher also allows the user to view their total progress through the training and allows them to print out a Certificate of Completion once they have viewed all of the materials. The Launcher opens the Player when the user selects a segment to view. The Launcher also allows a user to view other supporting materials e.g. PDF documents, non-certified training in the form of multimedia based players, etc.

The Player is a custom program built using HTML, JavaScript and ActionScript. The Player embeds Adobe (Macromedia) Flash objects that display the Video and PowerPoint Slides or other graphics. The Player contains all of the Watch Code functionality and code; logic to view, advance, or replay "sections" within a segment; and logic to launch the next segment (without having to go back to the launcher page). The Player tracks the users progress through the segments/sections and reports it back to the Server.

DETAILED DESCRIPTION OF THE PREFERRED EMBODIMENT

A system and method according to the present invention is described herein below and can be appreciated by reference to the accompanying drawings. Certain aspects may be commonly appreciated, and require no detailed discussion. For example, in order for a computer mediated training system to function, there must be a computing device and CPU element, and connection of the computing device to a network.

The System is comprised of the Server, the Launcher, and the Player. The Server is the system that contains the database and all of the data needed to support the launcher and the player (see below). The server also contains all of the code that supports the launcher and the player.

The Launcher is a page where all of the Topics and Presentations that make up a meeting (or event) are organized and presented to the user. It is primarily an organized view of the meeting or event content in a logical order and allows the user to navigate. The Launcher is where the user can see which segments they have viewed and which segments come next. The launcher also allows the user to view their total progress through the training and allows them to print out a Certificate of Completion once they have viewed all of the materials. The Launcher opens the Player when the user selects a segment to view. The Launcher also allows a user to view other supporting materials e.g. PDF documents, non-certified training in the form of multimedia based players, etc.

The Player is a custom program built using HTML, JavaScript and ActionScript. The Player embeds Adobe (Macromedia) Flash objects that display the Video and PowerPoint Slides or other graphics. The Player contains all of the Watch Code functionality and code; logic to view, advance, or replay "sections" within a segment; and logic to launch the next segment (without having to go back to the launcher page). The Player tracks the users progress through the segments/sections and reports it back to the Server.

The system also logically includes one or more display means for a Viewer or User to view the audio-visual training (also referred to herein as media, or media training). The invention taught herein provides a means for verifying that media training has been viewed.

Figure 1:
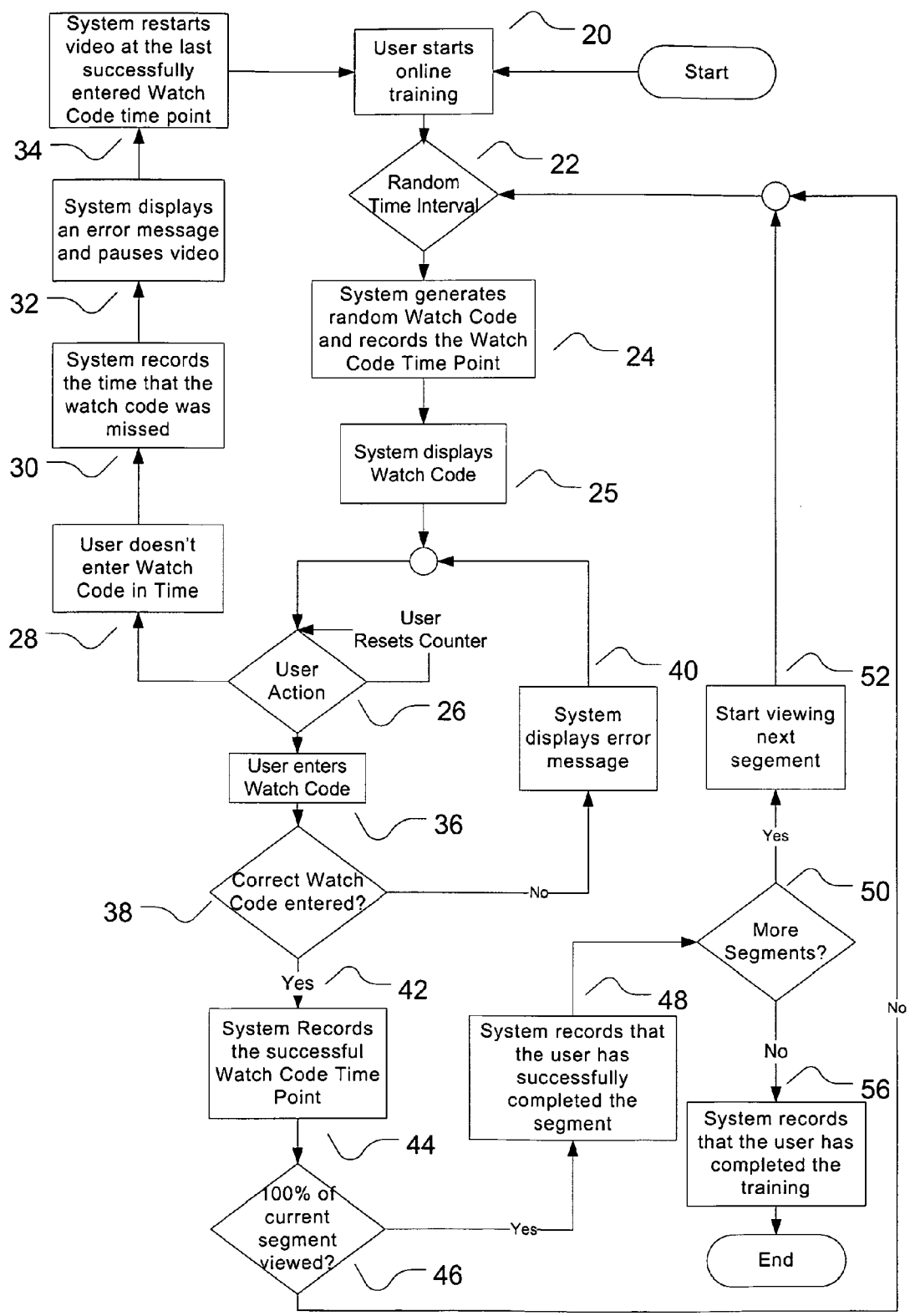
FIG. 1 depicts, by means of a flow chart, a system and method according to the preferred embodiment.

FIG. 1 is a diagram of the invention, describing the logical sequence supporting verification that an on-line media training has been viewed. Applicants refer to the inventive system in the preferred embodiments as having a "Watch Code" or "Watch Code Logic." As can be appreciated by reference to FIG. 1, a User or viewer commences on-line media training and the inventive system ultimately records that the User has completed the viewing of the media training As can be appreciated by reference to FIG. 1, the system of the invention taught herein begins with a User (also referred to herein as "viewer") commences a selected media training for on line training, and ends when the System has recorded that User has completed the media training.

Figure 3:
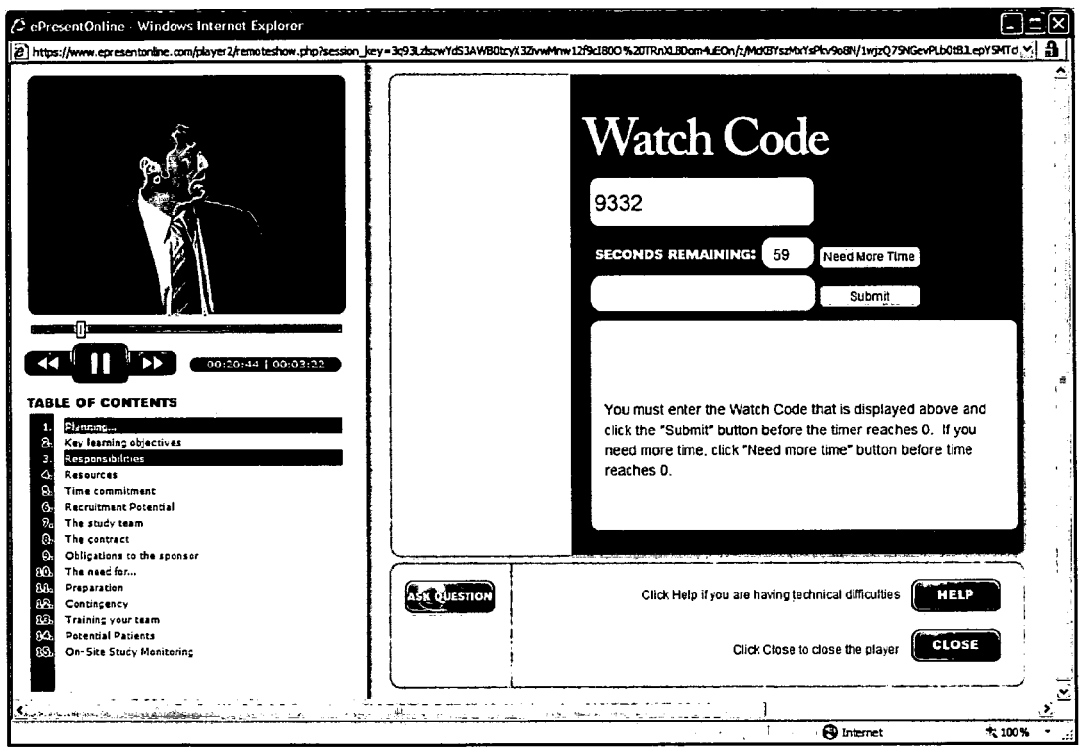
FIG. 3 is a screen shot illustrating Watch Code screen shot according to the preferred embodiment.
Figure 5:
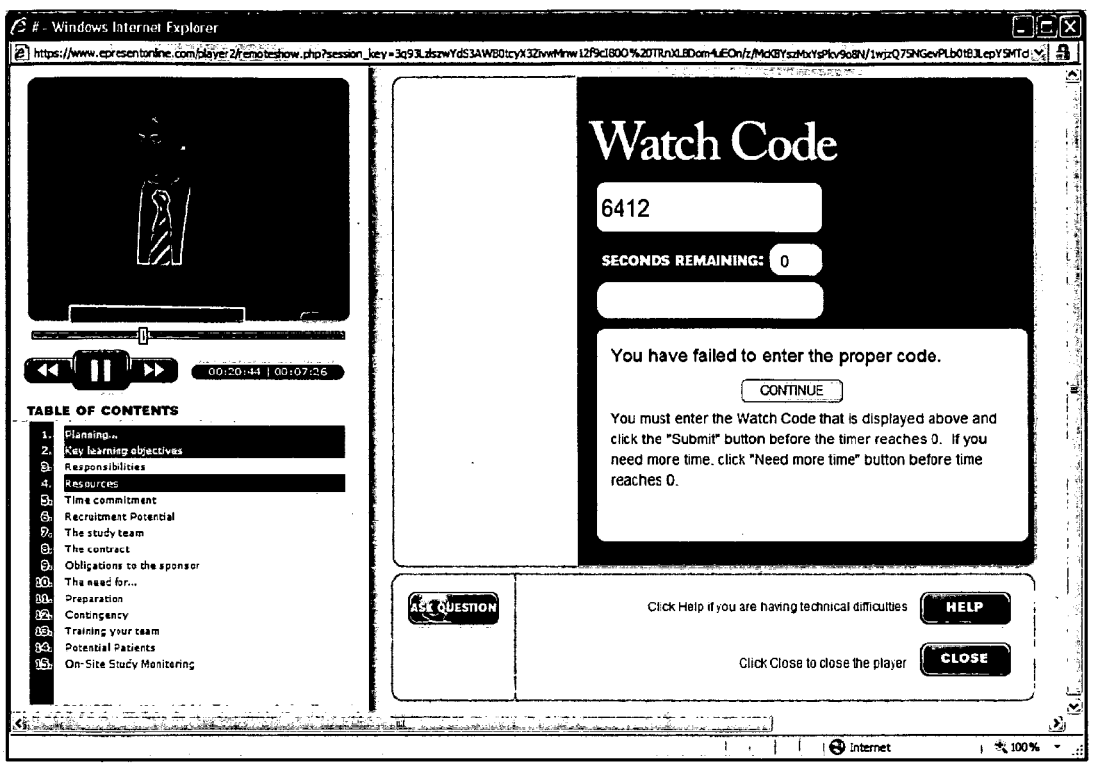
FIG. 5 is a screen shot illustrating a screen shot after failure to enter Watch Code according to the preferred embodiment.

The steps are as follows:

Viewer/User starts online training 20; this includes logging in to the system, providing user id information, according to the protocol design of the embodiment. In the preferred embodiment, the Viewer would be a physician required to complete the viewing of a recorded Investigator Meeting. As part of the preparation of the curriculum, the recording, which may total twenty or more hours of presentation, has been organized into logical portions or segments. From the User log-in, the system will track the segments successfully completed by the Viewer by means of the successful Watch Code Entry history. At some random time interval 22, a WatchCode is randomly generated 24 and the time point recorded. In the preferred embodiment, a WatchCode is a four digit number that appears on the screen. The WatchCode remains in the screen for a predetermined capture period 25, during which time the Viewer must type in the code. In the preferred embodiment, the capture period is 60 seconds. During the capture period, the content continues to play so long as the WatchCode is on the Screen (see FIG. 3). User action 26 serves to add an additional 60 seconds to the counter. If, as depicted in FIG. 5, the User fails to enter the Watch Code in the allotted time 28, the system, records the Watch Code as "missed" 30, displays a message to user and pauses the content 32. In the preferred embodiment, the user must click to continue, and the system will re-start, when the user clicks, at the last successfully entered Watch Code 34.

Figure 4:
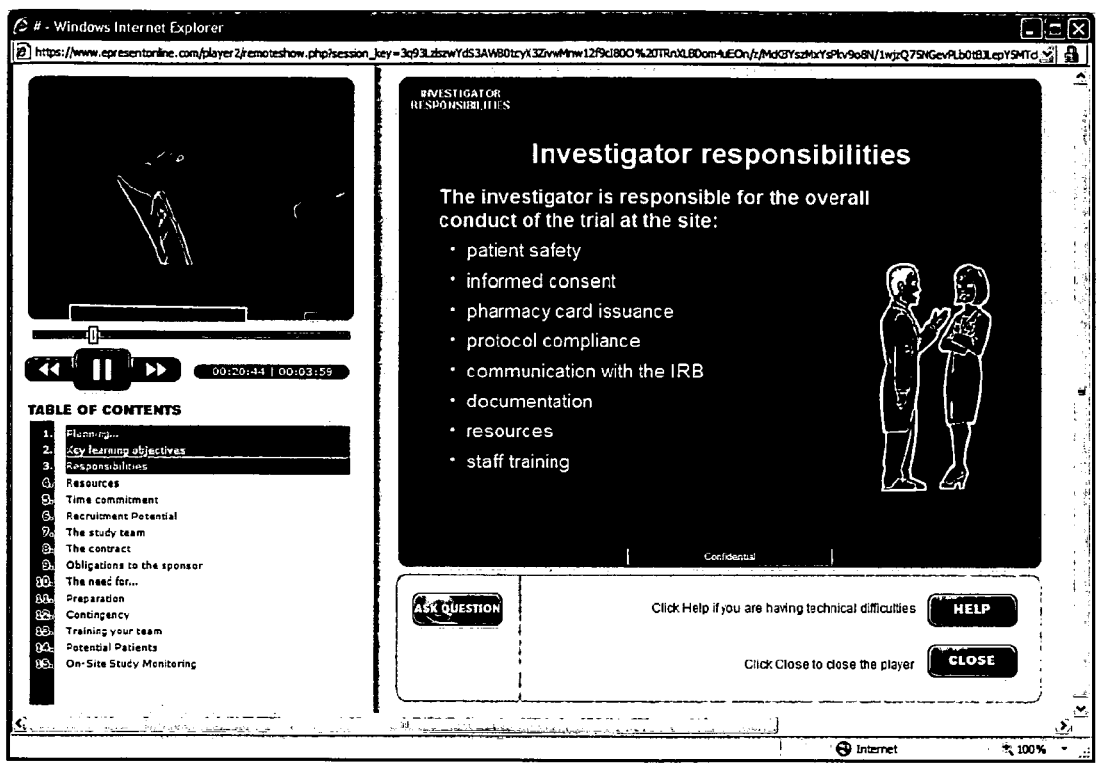
FIG. 4 is a screen shot illustrating a screen shot after successful entry of Watch Code according to the preferred embodiment.
Figure 6:
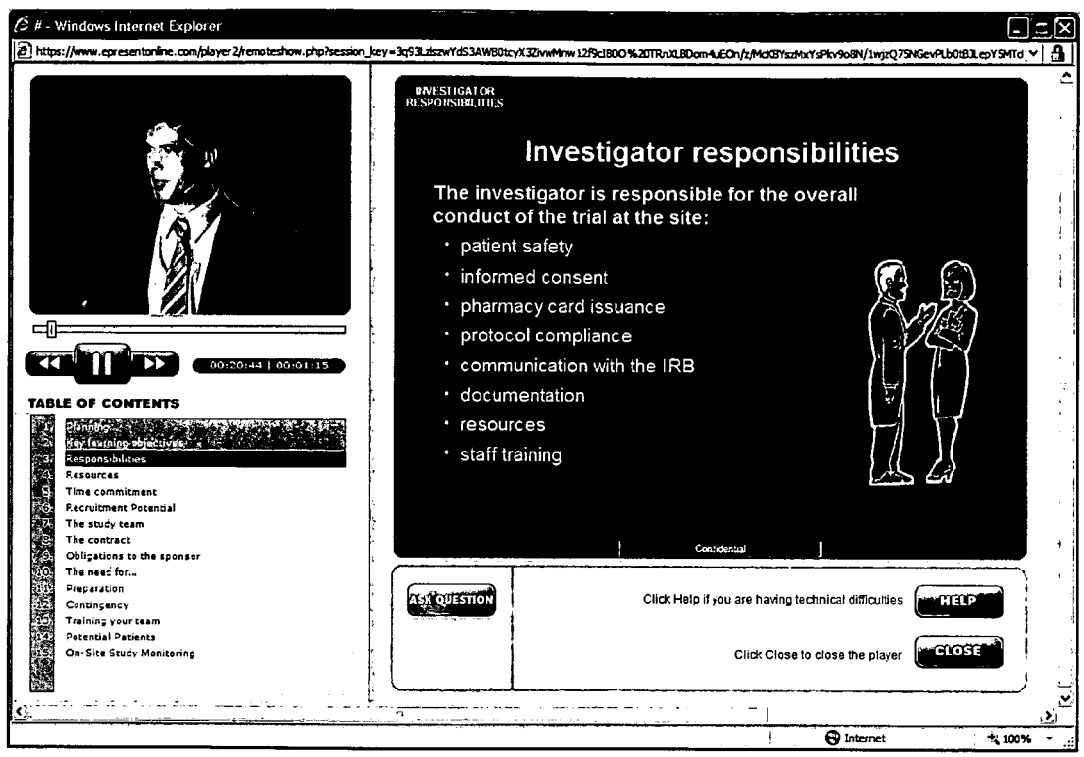
FIG. 6 is a screen shot illustrating a return to a presentation point after the last successful Watch Code entry according to the preferred embodiment.
Figure 7:
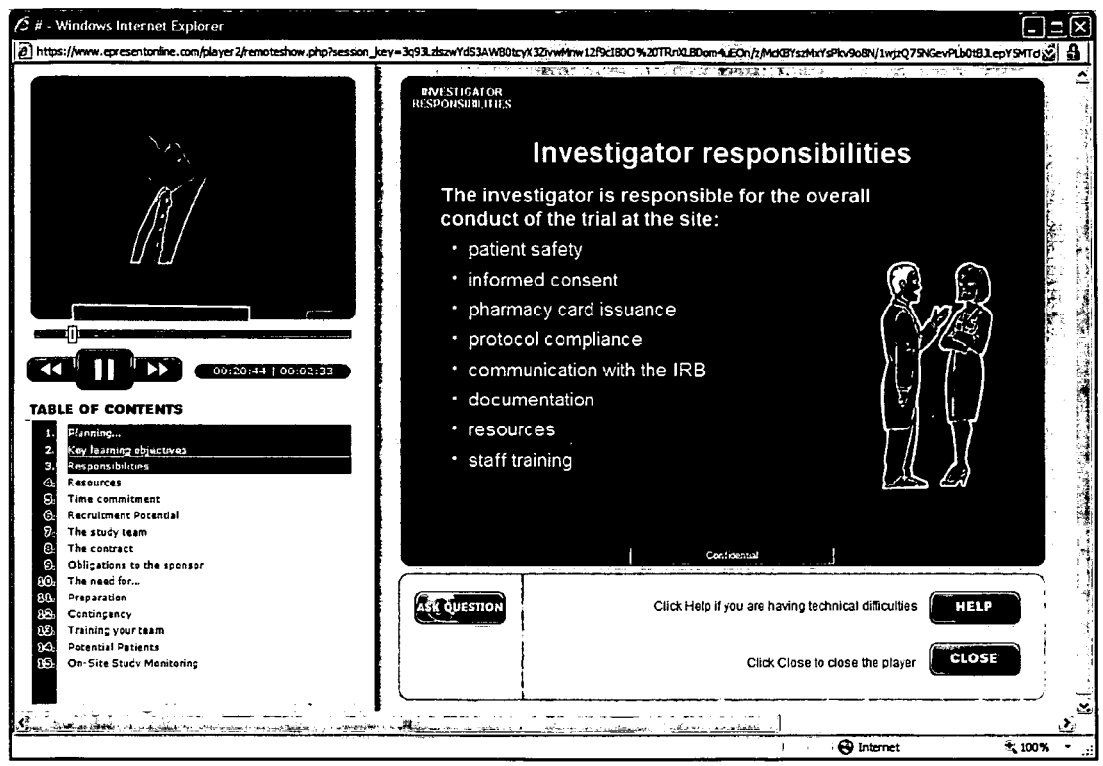
FIG. 7 is a screen shot according to the invention.

As depicted in FIG. 4, when a User enters Watch Code 36 the system checks if the number entered matches the code appearing on the screen 38. If incorrect, an error message appears, and User s asked to re-enter the Watch Code. If the code entered is correct 42, (see also FIG. 6), then the System records the successful Watch Code Time Point 44; if the entire current segment has not been viewed 46, if unviewed segments remain, return to step 22. If the entire segment has been viewed, the System records that the user has successfully completed the segment 48. The system checks: Are there more training segments 50? If yes, then Next segment begins 52; if no more training segment remain unviewed 54, then the system records the User has completed the training.

For any material to which the invention may be applied, an online training curriculum is created and defined. The audio and/or video and accompanying text and graphics are created. One or more training segments are defined for the curriculum. In the preferred embodiment, the training curriculum is the media recordation of an Investigator meeting, prefatory to a clinical trial. After audio-visual recordation of the Investigator meeting, text and graphic are Prepared, synchronized and integrated into the online training session. It can be appreciated that recording of an Investigator Meeting may be, in whole or in part, accomplished at "live" or "in person" Investigator Meeting, or through a presentation of the Investigator Meeting content—topics and presentations—(collectively, Investigator Meeting "Materials")—without an audience.

In the preferred embodiment, where delivery of the training material via the Internet is desired, the completed and formatted training materials are made available on-line. Once the material to be viewed is available, a viewer who is enrolled or otherwise registered for the on-line training logs in, is identified according to log-in information, and then may access the system to deliver the training via a network or the Internet.

Figure 2:
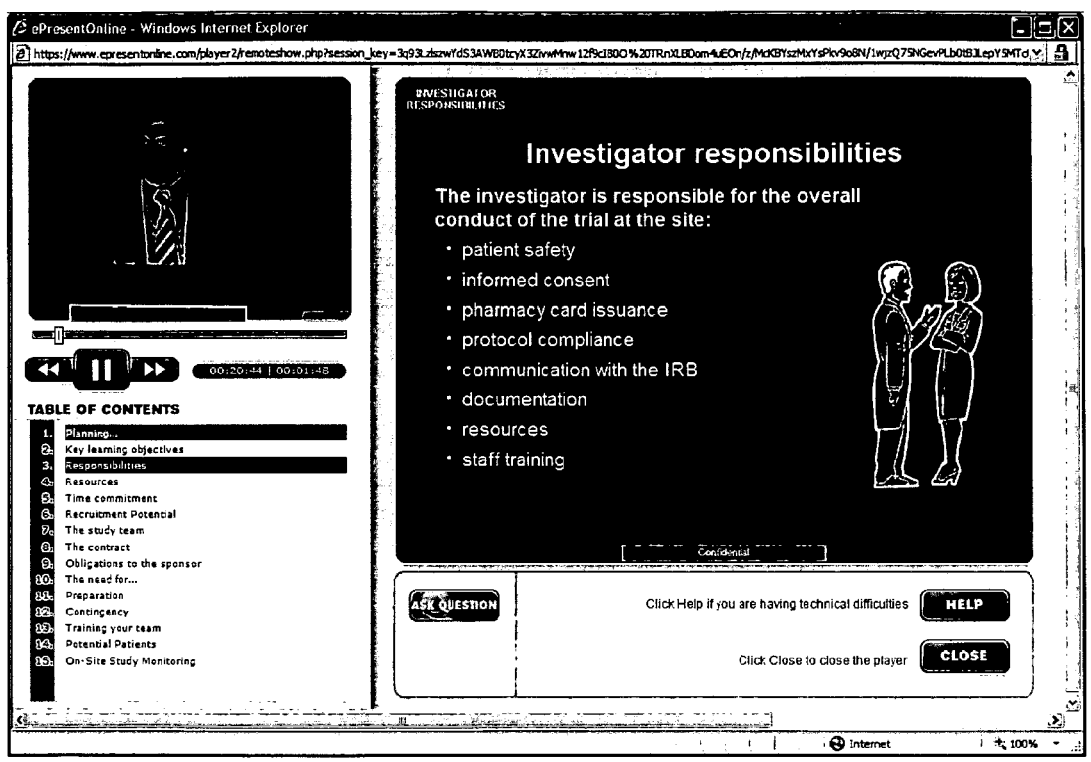
FIG. 2 is a screen shot illustrating a presentation screen according to the preferred embodiment.

In the preferred embodiment, the viewer starts training, after averring to be the person to whom the login information has been provided. The system starts playing the audio, and/or video for the training segment in the curriculum and displays any text or graphics that accompany the audio, and/or video. An exemplar of a screen shot representative of an on-line audio-visual training video is provided in FIG. 2. The system starts the training at the beginning of the first training segment unless the viewer has started the training previously, in which case the system restarts the training at the time point in the training segment where the previous viewing session ended.

After commencement of the training and at random intervals, the system generates and displays and a random code and requires the viewer to enter the displayed code within a configurable, set period of time (e.g. 60 seconds). The audio and/or video does not pause or stop during the time that the code to be entered is displayed on the screen.

When the viewer successfully enters the displayed code, the system records the time point of the successful entry and continues to play the audio and/or video and display all accompanying text and graphics.

If the viewer fails to enter the displayed code ("Watch Code") within the available period of time for whatever reason (i.e. because the viewer is not paying attention or is not physically at the computer or terminal), the system pauses the audio and/or video playback and waits for the viewer to return and elect to continue the training. Upon the viewer electing, by means of a keystroke, to continue the training, the system takes the viewer back to the time point where the last successful code entry occurred, requires them to re-watch the training from that point, and forward through random additional Watch Codes.

In the event that the viewer closes the browser or application without electing to continue, the system persists the last successfully entered display code time point. When training is resumed, the system restarts the training at that point.

When the system determines that the viewer has successfully watched all of the material for the current training segment, the system allows the viewer to proceed to the next training segment. In the event that the viewer wishes to re-review a successfully completed segment, the system does not generate or display random codes since the viewer has already been verified as having watched the entire training segment.

Once the viewer has completed watching all of the materials in all of the training segments, the system records the fact that the viewer has successfully completed the training. Advantages of the inventive system and method include, but are not limited to the following. The system does not require any administrator or teacher interaction during the training or require anything to be created beyond the training materials. The system does not provide any audible cues to a viewer who is not sitting at the computer and paying attention that the display code requires data entry. This prevents a viewer from simply starting the training and walking away while the training materials play. It also prevents the viewer from minimizing or hiding the training material while they perform other tasks on the computer or terminal.

The system actively tracks and records the watched portions of the training materials, ensuring that 100% of the training materials have been viewed. The system provides full audit/reporting capabilities about the progress for each individual viewer and allows detailed analysis of their progress through the training. The system allows a viewer to complete the viewing of the training materials over any number of viewing sessions, tracking automatically portions viewed, relieving viewer of personally tracking or recalling viewing history.

The system decouples the watching/viewing of training materials from the verification that the viewer has retained knowledge or can demonstrate proficiency in the area of training. This follows the traditional "learn then test" model. The system facilitates viewers procession through the training in a prescribed sequence. This ensures the tracking and recording of the satisfaction of pre-requisites, such as verified viewing of prepared audio-visual material. The system can allow a viewer to view the materials comprising a media package or program in any order, and confirm or verify that the viewer has watched all of the materials in the media package.

Alternate embodiments of the inventive system and method include, but are not limited to embodiments recited herein below.

The system can be offered in a stand-alone system where the training materials are distributed on physical media and not through the network or Internet. Instead of requiring data entry of a randomly generated code, the system can require a biometric input such as fingerprint, facial recognition, etc. through the use of a biometric hardware dongle or embedded biometric data acquisition device. The viewer can be required to submit their biometric profile at the beginning of the session and then be required to revalidate that biometric input at random intervals throughout the session.

A group of viewers can be created and watch the training as a group while the system tracks each viewer individually for completion status. In this implementation, each viewer in the group is required to "sign in," authenticating that each viewer is present, each time that training is conducted.

What is claimed is:

1. A computer-mediated media delivery and session viewing verification system optimized for physician compliance with requirements for participation as an Investigator in at least one clinical trial, said system comprising:
   a Server, said Server including at least one central processing unit, and storing video and/or audio of said Investigator Meeting content, where said content
      the content of the Investigator Meeting associated with said clinical trial, where said content includes Investigator Meeting topics and presentations, and where said Investigator Meeting may be in progress such that said content is dynamically acquired, and where physician attendance at said Investigator Meeting prefatory to clinical trail participation may be satisfied by exposure to a multimedia rendering of said Investigator Meeting;
   said Server also containing
      a database, and
      computer implementable instructions sufficient to Launcher and Player, said Server tracking and recording said physician compliance with requirements for participation as an Investigator in said clinical trial, and further providing information storage, where said stored information includes auditing and reporting of the progress of each physician, enabling detailed analysis of said progress;
   a Launcher, said Launcher comprising computer implementable instructions for a graphical user interface, and providing a navigable means for physician to view and select Investigator Meeting topics and presentations, where said selection is identified as a selected session, and including, for any selected session, accompanying session-related Investigator Meeting materials in a variety of forms;
   a Player, said Player comprised of computer implementable instructions for a graphical user interface and display, said instructions including
      providing a controllable means to display Investigator Meeting materials, and
      providing Watch Code functionality and logic, said Watch Code providing a means wherein during the computer-mediated media session delivery of a selected session, random prompts occur for physician input at random intervals during the selected session, such that if said input is successful, said selected session continues,
      and if said input is unsuccessful, said selected session re-sets to the last previously successful input, where such re-set is without recourse to the Launcher so that any number of interruptions may occur in the course of a selected session and said System automatically keeps track, aiding physician in the completion of said selected session, and storing the completion data in said Server thereby aiding in Clinical Trial commencement attributable to satisfaction of required physicians attending an Investigator Meeting.

* * * * *